(12) United States Patent
Haas et al.

(10) Patent No.: US 7,169,945 B2
(45) Date of Patent: Jan. 30, 2007

(54) PROCESS FOR THE EPOXIDATION OF OLEFINS

(75) Inventors: Thomas Haas, Frankfurt (DE); Willi Hofen, Rodenbach (DE); Wolfgang Wöll, Maintal (DE); Claudia Brasse, Hanau (DE); Guido Stochniol, Gelnhausen (DE); Norbert Ullrich, Essen (DE)

(73) Assignees: Degussa AG, Düsseldorf (DE); Uhde GmbH, Dortmund (DE)

( * ) Notice: Subject to any disclaimer, the term of this patent is extended or adjusted under 35 U.S.C. 154(b) by 75 days.

(21) Appl. No.: 10/724,300

(22) Filed: Nov. 26, 2003

(65) Prior Publication Data

US 2004/0110970 A1 Jun. 10, 2004

Related U.S. Application Data

(60) Provisional application No. 60/428,934, filed on Nov. 26, 2002.

(51) Int. Cl.
C07D 301/12 (2006.01)
(52) U.S. Cl. ..................................................... 549/531
(58) Field of Classification Search ................. 549/531
See application file for complete search history.

(56) References Cited

U.S. PATENT DOCUMENTS

| | | | |
|---|---|---|---|
| 2,870,171 A | 1/1959 | Gable | |
| 4,410,501 A | 10/1983 | Taramasso et al. | |
| 4,833,260 A | 5/1989 | Neri et al. | |
| 4,999,179 A | 3/1991 | Sugihara et al. | |
| 5,523,426 A | 6/1996 | Jubin, Jr. et al. | |
| 5,591,875 A | 1/1997 | Chang et al. | |
| 5,599,955 A | 2/1997 | Vora et al. | |
| 5,620,935 A | 4/1997 | Thiele | |
| 5,675,026 A | 10/1997 | Thiele | |
| 5,760,253 A | 6/1998 | Danner et al. | |
| 5,849,937 A | 12/1998 | Jubin, Jr. et al. | |
| 5,849,938 A | 12/1998 | Rueter et al. | |
| 5,912,367 A | 6/1999 | Chang | |
| 6,042,807 A * | 3/2000 | Faraj | 423/704 |
| 6,063,941 A | 5/2000 | Gilbeau | |
| 6,372,924 B2 | 4/2002 | Thiele | |
| 6,429,322 B1 | 8/2002 | Catinat et al. | |

FOREIGN PATENT DOCUMENTS

| | | |
|---|---|---|
| DE | 196 23 611 | 12/1997 |
| DE | 197 23 950 | 12/1998 |
| DE | 197 54 185 | 2/1999 |
| DE | 198 35 907 | 2/2000 |
| DE | 199 36 547 | 2/2001 |
| DE | 100 26 363 | 11/2001 |
| EP | 0 100 118 | 2/1984 |
| EP | 0 100 119 | 2/1984 |
| EP | 0 133 510 | 2/1985 |
| EP | 0 230 349 | 7/1987 |
| EP | 0 230 949 | 8/1987 |
| EP | 0 425 893 | 5/1991 |
| EP | 0 568 336 | 11/1993 |
| EP | 0 568 337 | 11/1993 |
| EP | 0 583 828 | 2/1994 |
| EP | 0 645 473 | 3/1995 |
| EP | 0 659 473 | 6/1995 |
| EP | 0 712 852 | 5/1996 |
| EP | 0 719 768 | 7/1996 |
| EP | 0 757 043 | 2/1997 |
| EP | 0 757 045 | 2/1997 |
| EP | 0 795 537 | 9/1997 |
| EP | 0 827 765 | 3/1998 |
| EP | 0 930 308 | 7/1999 |
| EP | 0 936 219 | 8/1999 |
| EP | 0 940 393 | 9/1999 |
| EP | 1 072 599 | 1/2001 |
| EP | 1 072 600 | 1/2001 |
| EP | 1 122 248 | 8/2001 |
| EP | 1 138 387 | 10/2001 |
| EP | 1 167 290 | 7/2002 |
| EP | 1 221 442 | 7/2002 |
| FR | 2 810 981 | 1/2002 |

(Continued)

OTHER PUBLICATIONS

Haas, T. et al 'Process for the expxidation of olefins with hydrogen peroxide in the presence of titanium zeolites' CA 141:7630 (2004).*

(Continued)

*Primary Examiner*—Amelia A. Owens
(74) *Attorney, Agent, or Firm*—Smith, Gambrell & Russell, LLP

(57) ABSTRACT

A process for the catalytic epoxidation of olefins in the presence of a titanium containing zeolite catalyst and a polar solvent whereby the deactivation of the catalyst upon recycling of the solvent has been considerably reduced. In the process one or more nitrogen containing compounds are introduced at some stage, a solvent stream is recovered, treated to contain less than 50 wppm nitrogen in the form of organic nitrogen compounds and at least a part of it is recycled to the epoxidation step. Also disclosed is a process for the catalytic epoxidation of propene which integrates the treatment and recycle of the solvent into the workup of the reaction mixture.

52 Claims, No Drawings

FOREIGN PATENT DOCUMENTS

| | | |
|---|---|---|
| JP | 2166636 | 6/1990 |
| WO | WO 97/47613 | 12/1997 |
| WO | WO 97/47614 | 12/1997 |
| WO | WO 98/47645 | 10/1998 |
| WO | WO 99/01445 | 1/1999 |
| WO | WO 99/07690 | 2/1999 |
| WO | WO 99/08985 | 2/1999 |
| WO | WO 99/11639 | 3/1999 |
| WO | WO 99/14208 | 3/1999 |
| WO | WO 99/23052 | 5/1999 |
| WO | WO 00/07695 | 2/2000 |
| WO | WO 00/17178 | 3/2000 |
| WO | WO 00/25881 | 5/2000 |
| WO | WO/76989 | 12/2000 |
| WO | WO 01/57009 | 8/2001 |
| WO | WO 01/57010 | 8/2001 |
| WO | WO 01/57012 | 8/2001 |
| WO | WO 01/68623 | 9/2001 |
| WO | WO 01/92242 | 12/2001 |
| WO | WO 02/00634 | 1/2002 |
| WO | WO 02/00635 | 1/2002 |
| WO | WO 02/02544 | 1/2002 |
| WO | WO 02/02545 | 1/2002 |
| WO | WO 02/14298 | 2/2002 |
| WO | WO 02/14299 | 2/2002 |

OTHER PUBLICATIONS

Paparatto, G. et al 'Integrated process for the preparation of olefin oxides' CA 136:184272 (2002).*

Ponceau, M. et al 'Production of epoxides by epoxidation of olefins with regeneration of catalyst' CA 134:147992 (2001).*

Goor, G. et al., "Ullmann's Encyclopedia of Industrial Chemistry, Fifth Edition," 1989, pp. 447-457, vol. A 13, XP-002233848, VCH Verlasgesellschaft, Weinheim, Germany (11 pages).

* cited by examiner

PROCESS FOR THE EPOXIDATION OF OLEFINS

REFERENCE TO A RELATED APPLICATION

This application claims the benefit of our copending provisional patent application 60/428,934 filed Nov. 26, 2002 which is relied on and incorporated herein by reference.

INTRODUCTION

The present invention relates to an improved process for the epoxidation of olefins using a titanium containing zeolite catalyst whereby the deactivation of the catalyst upon recycling of the solvent has been considerably reduced.

BACKGROUND OF THE INVENTION

From EP-A 100 118 it is known that olefins can be converted with hydrogen peroxide to epoxides when a titanium containing zeolite is used as catalyst. The reaction is preferably carried out in the presence of a polar solvent which dissolves both the olefin and the hydrogen peroxide in the reaction mixture. Methanol is preferably used as solvent.

Nitrogen containing compounds are frequently introduced into the process as components of the starting materials, as additives to the epoxidation reaction or as additives or auxiliaries during the work-up of the reaction mixture.

Nitrogen containing compounds may be introduced with the hydrogen peroxide used. Commercial hydrogen peroxide solutions often contain nitrogen containing compounds as peroxide stabilizers or as corrosion inhibitors. One example is Aminotrimethylenephosphonic acid used as a stabilizer.

Nitrogen containing compounds can be added to the epoxidation reaction to improve the propylene oxide selectivity. A large range of nitrogen containing compounds has been described for this purpose in available publications; for example: Ammonia, ammonium salts and nitrates in EP-A 230 949 and EP-A 712 852, organic nitrogen bases such as amines in EP-A 1 072 599 and WO 00/17178, amine oxides in WO 00/17178, carboxylic acid amides in EP-A 940 393 and WO 01/92242 and nitriles in WO 01/68623. In a similar fashion, nitrogen containing chelating agents have been added to the epoxidation mixture to suppress the decomposition of hydrogen peroxide as described in EP-A 757 045. All of these listed publications are relied on and incorporated herein for their disclosures of nitrogen compounds.

An example for introducing a nitrogen containing compound during the work-up of the epoxidation mixture is disclosed in WO 99/14208, incorporated herein by reference, where nitrobenzene is described as the solvent for the extraction of the olefin oxide from the reaction mixture.

When the epoxidation process is performed on an industrial scale the polar solvent used in the epoxidation reaction has to be recovered in the work-up of the reaction mixture and recycled to the epoxidation reaction for economic reasons. Processes for the recovery of the solvent have been described in WO 99/07690, WO 99/08985, WO 99/11639, WO 02/02544, WO 02/02545, WO 02/14298, WO 02/00635, WO 99/14208, WO 99/23052, WO 02/00634, U.S. Pat. No. 5,599,955, WO 01/57009 and WO 01/57010. When the solvent is recycled, impurities contained in the recycled solvent may accumulate in the recycle up to undesirable levels. This problem has been addressed for the impurity acetaldehyde in WO 99/07690 and WO 99/08985 and for methyl formate in WO 02/02544 and WO 02/02545.

The recycled solvent may also contain impurities poisoning the epoxidation catalyst which leads to lower catalytic activity and a more rapid deactivation of the epoxidation catalyst when the recycled solvent is used in the epoxidation reaction. The inventors have observed such a catalyst poisoning when one or several nitrogen containing compounds were introduced at some stage of the oxidation process. The known methods for recovering and recycling the solvent have not addressed the problem of catalysts poisoning and offer no solution to this problem.

Therefore it is an object of the present invention to improve a process for the catalytic epoxidation of olefins in the presence of a titanium containing zeolite catalyst wherein one or more nitrogen containing compounds are introduced at some stage of the process to achieve an improved activity of the epoxidation catalyst when solvent is recovered and recycled to the epoxidation stage.

SUMMARY OF THE INVENTION

According to one embodiment of the invention a process for the catalytic epoxidation of olefins, is carried out wherein one or more nitrogen containing compounds are introduced at some stage of the process, by (i) reacting an olefin with hydrogen peroxide in the presence of a titanium containing zeolite catalyst and a polar solvent, (ii) recovering a stream comprising the polar solvent from the reaction product of step (i), (ii) treating the stream recovered in step (ii) to contain less than 50 wppm nitrogen in the form of organic nitrogen compounds and (iv) recycling at least part of the treated stream of step (iii) to the epoxidation step (i).

In a preferred embodiment of the process the treatment in step (iii) is an acid treatment.

In a more detailed aspect of the invention, the process is carried out for the catalytic epoxidation of propene, wherein one or more nitrogen containing compounds are introduced at some stage of the process and a) in a reaction step propene is reacted with hydrogen peroxide in the presence of a titanium silicalite catalyst and a solvent comprising methanol to obtain a product stream, b) the product stream from the reaction step (a) is optionally passed to a pressure release step, c) the product stream is then separated in a pre-evaporator having less than 20 theoretical separation stages into an overhead product containing propene, propene oxide and methanol, and into a bottom product containing methanol and water, 20 to 60% of the total amount of methanol introduced with the product stream being removed with the overhead product and the residue remaining in the bottom product, d) at least a part of the bottom product from step c) is treated to contain less than 50 wppm nitrogen in the form of organic nitrogen compounds and, optionally after partially removing water, e) at least a part of the treated product from step d) is recycled to the reaction step a).

DETAILED DESCRIPTION OF THE INVENTION

In the process for the catalytic epoxidation of olefins according to the invention, one or more nitrogen containing compounds are introduced at some stage of the process. If several nitrogen containing compounds are introduced they may be introduced either at the same stage or at different stages of the process. Introduction of the nitrogen containing compounds may be both on purpose or unintentionally. The nitrogen compounds suitable for purposes of this invention include those nitrogen compounds disclosed in the publications referred to above which have been expressly relied on for that purpose.

An unintentional introduction of one or more nitrogen containing compounds occurs if at least one of the starting materials olefin and hydrogen peroxide or the polar solvent used in the epoxidation reaction contains a nitrogen containing compound. One example is the use of a commercial hydrogen peroxide containing a nitrogen containing compound as an additive. Such additives are for example aminophosphonic acids used as peroxide stabilizers or nitrate salts used as corrosion inhibitors.

Nitrogen containing compounds may also be introduced to the process for a certain purpose. Additives, such as ammonia, amines, amine oxides, carboxamides or nitrites may be introduced into the epoxidation reaction to improve epoxide selectivity. Nitrogen containing chelating compounds may be introduced at the same stage to reduce peroxide decomposition. Nitrogen containing compounds may also be introduced during the work-up of the reaction mixture as solvents for example in extraction steps or extractive distillations. Nitrogen containing compounds containing an unsubstituted $NH_2$ group, preferably hydrazine, can be used during work-up to convert carbonyl compounds to less volatile products.

The nitrogen containing compounds introduced into the process may be converted to other nitrogen containing compounds by chemical reactions within the process. Such a reaction can be the oxidation with hydrogen peroxide both uncatalyzed or catalyzed by the titanium containing zeolite. Ammonia may be oxidized to hydroxylamine, nitrite or nitrate. Primary amines may be oxidized to substituted hydroxylamines, oximes or nitroalkanes. Secondary amines may be oxidized to substituted hydroxylamines. Tertiary amines may be oxidized to amine oxides. Ammonia or primary amines may also react with epoxides to give amino alcohols which in turn can be further oxidized. Hydroxylamine may react with carbonyl compounds formed in side reactions from the epoxide to give oximes. In a similar way hydrazine will react with carbonyl compounds to give hydrazones and azines. If the work-up of the reaction mixture contains a hydrogenation stage, oximes, hydrazones and azines will be converted to primary amines.

From the above it is evident that a stream comprising the polar solvent recovered from the epoxidation reaction mixture may contain a wide range of organic nitrogen compounds even if only inorganic nitrogen containing compounds are introduced into the process. Due to the large number of reactions and the complex network of reactions it is not possible to predict per se which organic nitrogen compounds will be present and in what amount.

The inventors have observed that surprisingly the recycling of the recovered polar solvent to the epoxidation step leads to a reduced activity of the epoxidation catalyst and a more rapid catalyst deactivation when one or more nitrogen containing compounds are introduced at some stage of the epoxidation process with a titanium containing zeolite catalyst.

It has now been found that the activity of the epoxidation catalyst can be increased and the catalyst deactivation can be reduced by treating the recovered stream comprising the polar solvent to contain less than 50 wppm nitrogen in the form of organic nitrogen compounds before recycling it to the epoxidation step (wppm=weight parts per million=mg/kg). Preferably, the recovered stream is treated to contain less than 30 wppm, more preferably less than 15 wppm and most preferably less than 10 wppm nitrogen in the form organic nitrogen compounds.

Organic nitrogen compounds are understood as being compounds that contain a covalent bond between a carbon and a nitrogen atom. The amount of nitrogen in the form of organic nitrogen compounds is preferably determined as the difference between the total amount of nitrogen and the amount of nitrogen in the form of inorganic nitrogen compounds. The total amount of nitrogen is preferably determined by the Kjeldahl method as described in DIN 53625 (German Industrial Standard) which is well understood in the art. The amount of nitrogen in the form of inorganic nitrogen compounds is preferably determined by ion chromatography detecting the individual inorganic nitrogen compounds. When the recovered solvent stream has been subjected to a destination step before recycling it to the epoxidation stage it will usually contain no inorganic compounds other than ammonia. Therefore it will be sufficient for practical purposes to determine the amount of nitrogen in the form of inorganic nitrogen compounds by determination of ammonium, either as such or in the form of ammonium salts.

For the purpose of the invention, the determination of nitrogen in the form of organic nitrogen compounds can be performed both continuously or discontinuously. When the determination is done at intervals, these can be both periodical intervals or irregular intervals. Usually it will be sufficient to determine the amount of nitrogen in the form of organic nitrogen compounds only when process parameters have changed.

The treatment of the recovered stream to contain less than 50 wppm nitrogen in the form of organic nitrogen compounds may comprise separation steps or chemical reactions. The treatment may also combine several separation steps or may combine separation steps with one or more chemical reactions. Suitable separation steps for the treatment are for example distillation, crystallization, extraction, absorption or membrane separations. All of these unit operations are well understood in this art. Suitable chemical reactions for the treatment are acid base reactions, selective oxidation of organic nitrogen compounds or selective reduction of organic nitrogen compounds. Preferably the treatment comprises an acid treatment of the recovered solvent stream.

In a preferred embodiment of the process of the invention, the treatment of the recovered stream is by an acid treatment comprising adding an acid to the recovered stream and subjecting the obtained mixture to a distillation step. In the distillation step a distillate is withdrawn comprising the polar solvent and containing less than 50 wppm nitrogen in the form of organic nitrogen compounds.

In another preferred embodiment of the process of the present invention, the treatment of the recovered stream is an acid treatment comprising subjecting the recovered stream to a continuously operated distillation and feeding a stream comprising an acid at a point above the feed point of the recovered stream to the distillation column. A product stream comprising the polar solvent and containing less than 50 wppm nitrogen in the form of organic nitrogen compounds is withdrawn from the distillation column at a point above the feed point of the acid containing stream, preferably at the top of the column.

The acid treatment of the recovered stream may be affected by any suitable acid such as a mineral acid, a carboxylic acid or an acidic ion exchanger in its protonated form. Suitable mineral acids are nitric acid, sulfuric acid, hydrochloric acid, phosphoric acid or perchloric acid. Preferred mineral acids are sulfuric acid and phosphoric acid. Carboxylic acids are preferably selected from C1 to C12 mono or dicarboxylic acids such as formic acid, acetic acid, propionic acid, butyric acid, pentanoic acid, hexanoic acid, heptanoic acid, octanoic acid, nonanoic acid, decanoic acid, undecanoic acid or dodecanoic acid, oxalic acid, malonic acid, succinic acid, glutaric acid, adipic acid, maleic acid or fumaric acid. The most preferred carboxylic acid is acetic acid.

For the acid treatment with an acidic ion exchanger in its protonated form, both strongly acidic ion exchangers and weakly acidic ion exchangers can be used. Preferred are strongly acidic ion exchangers containing $SO_3H$ groups and weakly acidic ion exchangers containing COOH groups. The acidic ion exchanger is preferably based on an organic polymer, such as crosslinked polystyrene, or an organic inorganic hybrid polymer, such as a polysiloxane. The acidic ion exchanger may be either a liquid, a gel type solid or a macroporous solid. In a preferred embodiment the treatment is effected by passing the recovered solvent stream through a fixed bed containing the acidic ion exchanger.

Using the process according to the invention, any olefin can be epoxidized, in particular olefins with 2 to 6 carbon atoms. The process according to the invention is most particularly suitable for the epoxidation of propene to propene oxide. For economic reasons it would be preferred for an industrial scale process to use propene not in a pure form but as a technical mixture with propane that as a rule contains 1 to 15 vol. % of propane. The olefin may be fed as a liquid as well as in gaseous form into the reaction system.

Hydrogen peroxide is preferably used as an aqueous solution containing 1 to 90% by weight, preferably 10 to 70% by weight of hydrogen peroxide. A hydrogen peroxide crude product obtained from the extraction step of the anthraquinone process and containing 30 to 45% by weight of hydrogen peroxide is most preferably used. Alternatively, hydrogen peroxide solutions in alcohols, preferably in methanol can be used. These alcoholic solutions can be prepared by reaction of hydrogen and oxygen in the presence of a noble metal catalyst and the alcohol.

Crystalline, titanium-containing zeolites, preferably those of the composition $(TiO_2)_x(SiO_2)_{1-x}$ where x is from 0.001 to 0.05 and having a MFI or MEL crystalline structure, known as titanium silicalite-1 and titanium silicalite-2, are suitable as catalysts for the epoxidation process according to the invention. Such catalysts may be produced for example according to the process described in U.S. Pat. No. 4,410,501 the entire disclosure of which is incorporated herein for that purpose. The titanium silicalite catalyst may be employed as a shaped catalyst in the form of granules, extrudates or shaped bodies. For the forming process the catalyst may contain 1 to 99% of a binder or carrier material, all binders and carrier materials being suitable that do not react with hydrogen peroxide or with the epoxide under the reaction conditions employed for the epoxidation. Extrudates with a diameter of 1 to 5 mm are preferably used as fixed bed catalysts.

The reaction is carried out in the presence of a polar solvent in order to increase the solubility of the olefin, preferably propene, in the liquid phase. Suitable as solvent are all polar solvents that are not oxidized or are oxidized only to a slight extent by hydrogen peroxide under the chosen reaction conditions, and that dissolve in an amount of more than 10 wt. % in water. Preferred are solvents that are completely miscible with water. Suitable solvents include alcohols such as methanol, ethanol or tert.-butanol; glycols such as for example ethylene glycol, 1,2-propanediol or 1,3-propanediol; cyclic ethers such as for example tetrahydrofuran, dioxane or propylene oxide; glycol ethers such as for example ethylene glycol monomethyl ether, ethylene glycol monoethyl ether, ethylene glycol monobutyl ether or propylene glycol monomethyl ether, and ketones such as for example acetone or 2-butanone. Alcohols are preferred as solvents, methanol is particularly preferred.

The olefin, the hydrogen peroxide solution and the polar solvent may be introduced into the reactor as independent feeds or one or more of these feeds may be mixed prior to introduction into the reactor. The olefin is preferably employed in excess relative to the hydrogen peroxide in order to achieve a significant consumption of hydrogen peroxide, the molar ratio of olefin, preferably propene, to hydrogen peroxide preferably being chosen in the range from 1.1 to 30. The solvent is preferably added in a weight ratio of 0.5 to 20 relative to the amount of hydrogen peroxide solution used. The amount of catalyst employed may be varied within wide limits and is preferably chosen so that a hydrogen peroxide consumption of more than 90%, preferably more than 95%, is achieved within 1 minute to 5 hours under the employed reaction conditions.

In one embodiment of the invention, the titanium silicalite catalyst is suspended in the reaction mixture during the reaction. In that case, the catalyst is used in the form of a powder or in the form of a suspendable granular material that has been produced by forming in a manner known per se, for example by spray drying or fluidized bed granulation. When using a suspended catalyst, mixing reactors, for example stirred tank reactors or recycle reactors, as well as non-mixing flow reactors, for example tubular flow reactors, may be used for the reaction. A cascade consisting of one to three mixing reactors and a non-mixing flow reactor connected downstream is preferably used.

In another embodiment of the invention, the titanium silicalite catalyst is used as a fixed bed over which a mixture of the feedstock materials is passed. In this case, the catalyst is used in the form of shaped bodies that have been produced in a manner known per se, for example by extrusion with the addition of binders.

When using a fixed bed catalyst, reactors with bubble column characteristics can be used, i.e. the reactor contains a continuous liquid phase and a dispersed gaseous phase flows through the reactor in up-flow mode. Alternatively, reactors with trickle bed characteristics can be used, i.e. the reactor contains a gas phase and a liquid phase flows through the reactor in down-flow mode.

In a particularly preferred embodiment of the present invention, the process is conducted in a fixed bed reactor and the following flow conditions are selected to maintain the catalyst bed in a trickle bed state:

$$G/\lambda < 2000 \ m/h$$

and $$L_\psi < 50 \ m/h,$$

wherein

G is the gaseous superficial velocity defined as the gaseous flow rate in $m^3/h$ in the continuous flow reactor divided by the cross-section of the catalyst bed in $m^2$, L is the liquid superficial velocity defined as the liquid flow rate in m³/h in the continuous flow reactor divided by the cross-section of the catalyst bed in m², $$\lambda = \left[\left(\frac{\rho_G}{\rho_W}\right)\left(\frac{\rho_L}{\rho_{Air}}\right)\right]^{1/2}$$

and $$\psi = \left(\frac{\sigma_W}{\sigma_L}\right) \cdot \left[\left(\frac{\mu_L}{\mu_W}\right)\left(\frac{\rho_W}{\rho_L}\right)^2\right]^{1/3}$$

$\rho_G$ is the density of the gaseous phase in g/cm³,
$\rho_L$ is the density of the liquid phase in g/cm³,
$\rho_W$ is the density of water in g/cm³,
$\rho_{Air}$ is the density of air in g/cm³,
$\sigma_W$ is the surface tension of water in dyn/cm,
$\sigma_L$ is the surface tension of the liquid phase in dyn/cm,
$\mu_L$ is the viscosity of the liquid phase in centipoise,
$\mu_W$ is the viscosity of water in centipoise.

The epoxidation reaction is preferably carried out at temperatures between 0 and 80° C., more preferably between 40 and 65° C. According to a most preferred embodiment of the present invention the epoxidation reaction is carried out in a fixed bed reactor equipped with cooling means and the temperature profile within the reactor is maintained such that the cooling medium temperature of the cooling means is at least 30° C. and the maximum temperature within the catalyst bed is 60° C. at the most, preferably 55° C.

The epoxidation reaction can be carried out at ambient or at elevated pressure depending on the olefin to be epoxidized. If the boiling point of the olefin is below the temperature chosen for the epoxidation reaction, the pressure is usually maintained at 5 to 50 bar, preferably 15 to 30 bar.

In a preferred embodiment of the invention, the conditions for the epoxidation reaction, that is temperature, pressure and the amounts of olefin, hydrogen peroxide and solvent, are chosen to obtain a multiphase reaction mixture comprising a liquid aqueous hydrogen peroxide rich phase containing the polar solvent and a liquid organic olefin rich phase. To ensure the formation of a second liquid organic olefin rich phase the amount of olefin has to be selected in excess of the amount soluble in the aqueous phase comprising water, hydrogen peroxide and solvent at the chosen temperature and pressure. Maintaining two immiscible liquid phases during the epoxidation reaction leads to improved epoxide selectivity.

In a preferred embodiment of the invention, ammonia is added to the epoxidation stage to improve the epoxide selectivity in an amount of 100 to 3000 ppm, preferably 300 to 2000 ppm based on the weight of hydrogen peroxide.

The recovery of the polar solvent from the epoxidation reaction mixture may be performed by any suitable separation method or combination of separation methods, such as distillation, crystallization, extraction, adsorption or the like. Preferably, a combination of distillation steps is used for the recovery. Also preferably, unreacted olefin and the epoxide product are separated from the solvent stream during the recovery process. Some of the water contained in the solvent stream may be separated as well during the solvent recovery. The recovered solvent stream, that is treated to contain less than 50 wppm nitrogen in the form of organic compounds, may comprise further components, such as water, unreacted hydrogen peroxide or byproducts from the epoxidation process.

A preferred embodiment of the invention is directed towards an improved process for the catalytic epoxidation of propene with hydrogen peroxide in the presence of a titanium silicalite catalyst and a solvent comprising methanol. The improved process integrates the inventive treatment and recycle of the solvent into the workup of the reaction mixture to provide propene oxide with a minimum of separation steps and a low energy requirement while at the same time maintaining high catalytic activity and a long catalyst lifetime.

Epoxidation of propene is carried out as described above using a solvent comprising methanol.

Before the working up stage the pressure of the propene epoxidation reaction mixture is preferably released in a pressure release stage to the pressure employed in the working up of the propene oxide. Part of the propene dissolved in the reaction mixture and possibly propane is gassed out. The resultant gas is recompressed via a compressor to the pressure prevailing in the reactor and is returned to the reaction.

The reaction mixture is then separated in a pre-evaporator into an overhead product containing propene, possibly propane, propene oxide and methanol, and into a bottom product containing methanol, water, higher boiling point byproducts, such as for example propylene glycol, unreacted hydrogen peroxide and possibly suspended titanium silicalite catalyst. The pre-evaporator according to the invention has less than 20, preferably at most 10 theoretical separation steps and is preferably designed so that the rectification section corresponds to a single distillation stage and the remaining separation effect is achieved in the stripping section. The pre-evaporator is operated at a reflux ratio of at most 1.5 and if desired may also be operated totally without reflux. The pressure in the pre-evaporator is preferably chosen in the range from 1.5 to less than 3 bar in order to avoid decomposition of hydrogen peroxide. The pre-evaporator is operated so that between 20 and 60% of the amount of solvent fed in with the reaction mixture is removed with the overhead product and the balance remains in the bottom product. Preferably, more than 95%, more preferably, more than 98% and most preferably, more than 99% of the propene oxide fed in is contained in the overhead product, and preferably, more than 90%, more preferably, more than 97% of the water fed in is contained in the bottom product.

The product stream fed to the pre-evaporator preferably contains 0.5 to 20% by weight of propene, 0 to 4% by weight of propane, 5 to 35% by weight of propene oxide, 35 to 80% by weight of methanol, 5 to 40% by weight of water, 0.1 to 8% by weight of higher boiling point byproducts, 0.1 to 5% by weight hydrogen peroxide and 0 to 5% by weight of titanium silicalite catalyst. This product stream is preferably separated in the pre-evaporator into an overhead product containing 1 to 40% by weight of propene, 0 to 10% by weight of propane, 15 to 75% by weight of propene oxide, 20 to 85% by weight of methanol and 0 to 5% by weight of water, and into a bottom product containing 0 to 2% by weight of propene oxide, 30 to 80% by weight of methanol, 15 to 65% by weight of water, 0.1 to 10% by weight of higher boiling point byproducts, 0.1 to 5% by weight of hydrogen peroxide, 0 to 10% by weight of titanium silicalite catalyst and more than 50 wppm nitrogen in the form of organic nitrogen compounds.

At least a part and preferably all of the bottom product of the pre-evaporator comprising methanol and water is treated to contain less than 50 wppm nitrogen in the form of organic nitrogen compounds. At least a part and preferably all of the resulting treated product is then recycled to the epoxidation reaction. Preferably at least a part of the water contained in the bottom product of the pre-evaporator is removed before the recycle stream is fed to the epoxidation stage. Removal of water may be performed before the treatment, after the treatment or combined with the treatment into a single process stage.

The treatment of the recovered methanol to contain less than 50 wppm nitrogen in the form of organic nitrogen compounds may be performed by all methods described above as suitable for the treatment of a recovered polar solvent stream. Preferably the treatment comprises an acid treatment of the recovered methanol stream. Most preferably, the same embodiments of the acid treatment are employed as described above as preferred embodiments for the acid treatment of the solvent stream.

In a preferred embodiment of the propene epoxidation process the overhead product from the pre-evaporator is at least partially condensed to give a condensate containing 0 to 12% by weight of propene, 0 to 5% by weight of propane, 15 to 75% by weight of propene oxide, 20 to 85% by weight of methanol and 0 to 8% by weight of water. Preferably the overhead product is only partially condensed and the uncondensed propene, possibly mixed with propane, is recompressed via a compressor to the pressure prevailing in the reaction part and is recycled to the reaction. The propene still dissolved in the condensate and possibly propane are preferably stripped out from the condensate in a C3 stripper. Preferably the stripped-out gas is recycled to the partial condenser. Preferably the partial condensation is performed in two steps. The overhead product from the pre-evaporator is partially condensed in a first condenser and the gaseous effluent from the first condenser is condensed in a second condenser maintained at a temperature below the temperature of the first condenser. Preferably the temperature within the first condenser is maintained at 40 to 70° C. and the temperature within the second condenser is maintained at 20 to 35° C. By using a two step condensation the amount of valuable propene oxide that can not be recovered is considerably reduced and the energy consumption for cooling is reduced compared to a one step condensation. When applying the two step condensation the condensates of both condensers are passed to the C3 stripper to remove constituents having a boiling point that is lower than that of propene oxide, whereby the gaseous effluent from the stripper is partially condensed in the second condenser and the condensate is recycled to the C3 stripper.

The condensate, obtained by at least partially condensing the overhead product from the pre-evaporator and optionally stripping it in a C3 stripper is then subjected to an extractive distillation with an aqueous extraction solvent. The condensate is fed to the middle section of a continuously operated distillation column. The aqueous extraction solvent is added to the extractive distillation column at a point above the point at which the condensate enters the column. A purified propene oxide is withdrawn at the top of the column. At the bottom of the extractive distillation column a bottom product containing methanol and water is obtained. This bottom product is combined with the bottom product from the pre-evaporator and the combined product is subjected to the treatment to remove organic nitrogen compounds.

The extraction solvent is preferably an aqueous hydrazine solution containing from 0.5 to 5% by weight hydrazine. When an aqueous hydrazine solution is used as the extraction solvent, the extractive distillation not only removes methanol but also acetaldehyde and other carbonyl compounds from the propene oxide and provides a purified propene oxide containing less than 50 ppm methanol and less than 50 ppm acetaldehyde in a single purification step.

The amount of the extraction solvent fed to the extractive distillation column is preferably chosen so that the mass ratio of the extraction solvent feed relative to the amount of methanol contained in the pre-evaporator condensate is in the range from 0.1 to 10. The extractive distillation is preferably operated at an absolute pressure from 1 to 5 bar, more preferably at an absolute pressure from 1.5 to 2.5 bar. The reflux ratio is preferably chosen in the range from 1 to 5.

The distillation column used for the extractive distillation comprises a stripping section between the column bottoms and the feed point of the pre-evaporator condensate, an extraction section between the feed point of pre-evaporator condensate and the feed point of the extraction solvent and a rectifying section between the feed point of the extraction solvent and the point where the purified propene oxide is withdrawn. Preferably a distillation column is used that has a separation efficiency of 10 to 30 theoretical stages in both the stripping section and the extraction section and a separation efficiency of 20 to 60 theoretical stages in the rectifying section. The distillation column can be a tray column containing discrete trays such as sieve trays or bubble cap trays. The distillation column can also be a packed column and both random packings as well as structured packings, such as metal gauze packings can be used. The distillation column may also combine sections with discrete trays and sections with packings. The extraction section is preferably designed with discrete trays.

In a preferred embodiment of the epoxidation process of the present invention, the bottom product from the pre-evaporator or the combined bottom products from the pre-evaporator and the extractive distillation are subjected to a catalytic hydrogenation step before being subjected to the treatment to remove organic nitrogen compounds. The additional hydrogenation step reduces the accumulation of byproducts, such as methyl formate and dimethoxymethane, in the solvent recycle and improves the purity of the propene oxide recovered with the process.

The catalytic hydrogenation is preferably carried out as a heterogeneous catalytic hydrogenation at a hydrogen partial pressure of 0.5 to 30 MPa. It is particularly preferred to conduct the hydrogenation step at a temperature in the range of 80° C. and 150° C., preferably 100° C. to 180° C. and at a hydrogen partial pressure of 1 to 25 MPa.

Suitable hydrogenation catalysts are selected from supported catalysts comprising one or more of metals selected from the group consisting of Ru, Rh, Pd, Pt, Ag, Ir, Fe, Cu, Ni and Co. Alternatively Raney Nickel and Raney Cobalt both optionally being doped with one or more of the above mentioned can be used. The catalyst support is preferably selected from activated carbon and metal oxides selected from $SiO_2$, $TiO_2$, $ZrO_2$ and $Al_2O_3$, mixed oxides comprising at least two of Si, Al, Ti and Zr and mixtures thereof.

The hydrogenation can be carried out continuously or batch-wise e.g., in a suspension method or a fixed-bed method. It is especially preferred to use a trickle-bed reactor. The fixed-bed catalysts to be used therein are preferably pellets with a diameter of 0.5 to 5 mm, especially 1 to 3 mm and with a length of 1 to 10 mm. The noble-metal content is in the customary range, preferably 0.5 to 5% by weight.

The advantages of the present invention will be apparent in view of the following examples which are illustrative of the embodiments of the invention.

EXAMPLES

Example 1 (Comparative Example)

Epoxidation was carried out continuously in a tubular reactor of 300 ml volume filled with silica bonded titanium-silicalite extrudates with a diameter of 3 mm. The equipment was furthermore comprised of three containers for liquids and relevant pumps and a liquid separating vessel. The three containers for liquids comprised methanol, 60 wt-% aqueous $H_2O_2$ and propene, respectively. The 60% $H_2O_2$ was adjusted with ammonia to a pH of 4.5. The reaction temperature was controlled via an aqueous cooling liquid circulating in a cooling jacket whereby the cooling liquid temperature was controlled by a thermostat. The reactor pressure was 25 bar absolute. Mass flow of the feeding pumps was adjusted to result in a propene feed concentration of 21.5 wt-%, a methanol feed concentration of 57 wt-% and an $H_2O_2$ feed concentration of 9.4 wt-%. The reactor was operated in down-flow operation mode. The cooling jacket temperature was 41° C., the total mass flow was 0.35 kg/h and the maximum temperature was 59° C. Product output was determined by gas chromatography and the $H_2O_2$ conversion by redox titration. The catalyst selectivity was calculated on the basis of gas chromatographical analysis of the propene oxygenates as the ratio of the amount of propene oxide formed relative to the amount of all propene oxygenates formed. Initial $H_2O_2$ conversion was 96% at a catalyst selectivity of 96%.

The reaction mixture obtained from the reaction after release of pressure was separated in a pre-evaporation stage into an overhead product containing propene, propane, propene oxide and methanol, and a bottom product containing methanol, propylene glycol monomethyl ethers, propylene glycol, water, high boiling point compounds and non-converted hydrogen peroxide. A liquid condensate that contains propene oxide and methanol as well as propene and propane dissolved therein was obtained from the vapour state overhead product. The uncondensed stream, which substantially consisted of propene and propane, was returned to the epoxidation reaction. The propene and propane dissolved in the condensate were stripped from the latter in a C3 stripper and returned in the vapour state together with the pre-evaporator overhead stream to the partial condensation stage. The stripped condensate stream, which consisted substantially of propene oxide and methanol and had been freed from propene and propane, was separated in an extractive distillation in which a 1.5 wt-% aqueous solution of hydrazine was fed in as extraction agent immediately underneath the head of the column, into a propene oxide purified product and into a bottom product that consisted substantially of methanol and water. The bottom product was combined with the bottom product obtained in the pre-evaporator and subjected to hydrogenation in a trickle-bed reactor for continuous hydrogenation. The hydrogenation reactor had an interior volume of 150 ml and was filled with a hydrogenation catalyst in form of extrudates with 2.3 mm diameter comprising 2% Ru on activated carbon (The catalyst was prepared according to the incipient wetness method using $RuCl_3$, "Preparation of Catalyst", Demon, B. et al., Elsevier, Amsterdam, 1976, page 13). The hydrogenation was performed at 140° C. and 40 bar abs. at a hydrogen flow rate of 10 ml/h.

The hydrogenated product was fed at a rate of 3.5 kg/h to the middle section of a methanol distillation column with 35 theoretical stages and was continuously distilled at a pressure of 2 bar abs. with a reflux ratio of 2. At the top of the column 2.5 kg/h of a methanol stream was obtained which contained more than 99 wt-% methanol, 0.13 wt-% water, 55 wppm total nitrogen and less than 5 wppm nitrogen from ammonia. Total nitrogen content was determined by the Kjeldahl method of DIN 53625, ammonia nitrogen by ion chromatography. From the difference of total nitrogen and ammonia nitrogen the nitrogen content from organic nitrogen compounds was calculated as between 50 and 55 wppm.

The recovered methanol was reused for the epoxidation of propene in a laboratory apparatus consisting of two tubular reactors in series with a diameter of 18 mm and a length of 300 mm each, each containing 8 g of the same catalyst as used in the first epoxidation. The catalyst had been previously conditioned by using it for propene epoxidation for more than 3000 h. The reactors were operated in up-flow mode at a pressure of 25 bar abs. and a temperature of 36° C. in the first reactor and 44° C. in the second reactor. Three feed streams were simultaneously introduced into the reactor. Feed 1 was a mixture of 715 g 60 wt-% aqueous hydrogen peroxide and 1420 g fresh methanol, the methanol containing no detectable amounts of nitrogen compounds, and was introduced at a rate of 22.5 g/h. Feed 2 was a mixture of 1284 g recovered methanol and 1.335 g 32 wt-% aqueous ammonia, introduced at a rate of 14.8 g/h. Feed 3 was propene, introduced at a rate of 23 g/h.

The reactor effluents were analyzed for propylene oxide by gas chromatography and for hydrogen peroxide by redox titration. Propylene oxide yield was calculated on the amount of hydrogen peroxide fed. The results are shown in table 1.

Example 2

Example 1 was repeated with the variation, that a 10 wt-% solution of acetic acid in methanol was fed to the reflux stream of the methanol distillation column at a rate of 81 g/h. The methanol stream withdrawn at the top of the column contained more than 98 wt-% methanol, 1.6 wt-% water, 33 wppm total nitrogen and 7 wppm nitrogen from ammonia. From the difference of total nitrogen and ammonia nitrogen the nitrogen content from organic nitrogen compounds was calculated as 26 wppm. Reuse of the recovered methanol for the epoxidation of propene as in example 1 gave the results shown in table 1.

Example 3

Example 1 was repeated with the variation, that a 10 wt-% aqueous solution of acetic acid was fed to the reflux stream of the methanol distillation column at a rate of 98 g/h. The methanol stream withdrawn at the top of the column contained more than 97 wt-% methanol, 2 wt-% water, 14 wppm total nitrogen and less than 4 wppm nitrogen from ammonia. From the difference of total nitrogen and ammonia nitrogen the nitrogen content from organic nitrogen compounds was calculated as between 10 and 14 wppm. Reuse of the recovered methanol for the epoxidation of propene as in example 1 gave the results shown in table 1.

Example 4

Example 1 was repeated and a methanol stream containing more than 97 wt-% methanol, 2.5 wt-% water and 110 wppm total nitrogen was withdrawn from the top of the methanol column. 1000 ml of this recovered methanol were treated with 10 ml Dowex 50X8 strongly acidic ion exchanger in the H$^+$-form at room temperature for 3 days with occasional shaking. The treated methanol contained 1.9 wppm total nitrogen. This treated recovered methanol was reused for the epoxidation of propene as described in example 1 with the difference, that recovered methanol was used in feed 1 in place of fresh methanol. The results are shown in table 1.

TABLE 1

| Example | Nitrogen in recovered methanol [mg/kg] | | | $H_2O_2$ conversion [%] | Propene oxide yield [%] |
|---|---|---|---|---|---|
| | Total | Ammonia | Organic | | |
| 1 | 55 | <5 | 50–55 | 26 | 18 |
| 2 | 33 | 7 | 26 | 49 | 36 |
| 3 | 14 | <4 | 10–14 | 54 | 42 |
| 4 | 1.9 | n.d. | <1.9 | 55 | 41 | n.d.: not determined

In comparative example 1 poisoning of the catalyst by the recycled methanol leads to low hydrogen peroxide conversion and low propene oxide yield. The use of a recovered methanol with a low content of nitrogen in the form of organic compounds in examples 2 to 4 results in increased catalyst activity as can be seen by the increased hydrogen peroxide conversion and propene oxide yield.

Further variations and modifications of the foregoing invention will be apparent to those skilled in the art and are intended to be encompassed by the claims appended hereto.

We claim:

1. Process for the catalytic epoxidation of olefins, comprising the steps of: (i) reacting an olefin with hydrogen peroxide in an epoxidation reaction in the presence of a titanium containing zeolite catalyst and a polar solvent to form a reaction product, (ii) recovering a stream comprising the polar solvent from the reaction product of step (i), (iii) treating the stream recovered in step (ii) to contain less than 50 wppm nitrogen in the form of organic nitrogen compounds to obtain a treated stream and (iv) recycling at least part of the treated stream of step (iii) to the epoxidation reaction step (i), wherein one or more nitrogen containing compounds are introduced at some stage of the process.

2. The process of claim 1, wherein the treated stream recycled in step (iv) contains less than 10 wppm nitrogen in the form of organic nitrogen compounds.

3. The process of claim 1, wherein the polar solvent is an alcohol.

4. The process of claim 3, wherein the alcohol is methanol.

5. The process of claim 1, wherein the olefin is propene.

6. The process of claim 1, wherein the titanium containing zeolite catalyst is a titanium silicalite with MFI or MEL structure.

7. The process of claim 1, wherein the epoxidation reaction of step (i) is conducted in the presence of 100 to 3000 ppm ammonia based on the weight of hydrogen peroxide.

8. The process of claim 7, wherein the epoxidation reaction is conducted in the presence of 300 to 2000 ppm ammonia based on the weight of hydrogen peroxide.

9. The process of claim 1, wherein the stream in step (iii) is treated with an acid treatment.

10. The process of claim 9, wherein the acid treatment comprises:
a) adding an acid to the stream recovered in step (ii);
b) subjecting the reaction product of step a) to distillation and
c) withdrawing a distillate comprising the polar solvent and containing less than 50 wppm nitrogen in the form of organic nitrogen compounds.

11. The process of claim 10, wherein the acid is a mineral acid.

12. The process of claim 11, wherein the mineral acid is selected from the group consisting of sulfuric acid and phosphoric acid.

13. The process of claim 10, wherein the acid is a carboxylic acid.

14. The process of claim 13, wherein the carboxylic acid is acetic acid.

15. The process of claim 9, wherein the acid treatment comprises:
a) subjecting the stream recovered in step (ii) to a continuously operated distillation;
b) feeding a stream comprising an acid at a point above a feed point of the stream recovered in step (ii) and
c) withdrawing a product stream comprising the polar solvent and containing less than 50 wppm nitrogen in the form of organic nitrogen compounds at a point above a feed point of the acid comprising stream.

16. The process of claim 15, wherein the acid is a mineral acid.

17. The process of claim 16, wherein the mineral acid is selected from the group consisting of sulfuric acid and phosphoric acid.

18. The process of claim 15, wherein the acid is a carboxylic acid.

19. The process of claim 18, wherein the carboxylic acid is acetic acid.

20. The process of claim 9, wherein the acid treatment comprises treating the stream recovered in step (ii) with an acidic ion exchanger in its protonated form.

21. The process of claim 20, wherein the stream recovered in step (ii) is passed through a fixed bed containing the acidic ion exchanger.

22. The process of claim 20, wherein the acidic ion exchanger is a strongly acidic ion exchanger.

23. The process of claim 22, wherein the strongly acidic ion exchanger contains $SO_3H$ groups.

24. The process of claim 20, wherein the acidic ion exchanger is a weakly acidic ion exchanger.

25. The process of claim 24, wherein the weakly acidic ion exchanger contains COOH groups.

26. The process of claim 1, wherein the nitrogen containing compound is present in step (i) by being contained in at least one of the olefins, hydrogen peroxide, and polar solvent.

27. The process of claim 1, wherein the nitrogen containing compound is added to the epoxidation reaction.

28. The process of claim 1, wherein the nitrogen containing compound is added in step (ii).

29. The process of claim 1, wherein the nitrogen containing compound is introduced during at least one of steps (i) to (iii) or between any two of such steps.

30. Process for the catalytic epoxidation of propene, comprising
a) in a reaction step reacting propene with hydrogen peroxide in the presence of a titanium silicalite catalyst and a solvent comprising methanol to obtain a product stream,
b) optionally passing the product stream from the reaction step to a pressure release step,
c) separating the product stream in a pre-evaporator having less than 20 theoretical separation stages into an overhead product containing propene, propene oxide and methanol, and into a bottom product containing methanol and water, removing 20 to 60% of the total amount of methanol introduced with the product stream with the overhead product and the rest remaining in the bottom product, d) treating all or a part of the bottom product from step c) to contain less than 50 wppm nitrogen in the form of organic nitrogen compounds and, optionally after partially removing water, e) recycling all or a part of the treated product from step d) to the reaction step a), wherein one or more nitrogen containing compounds are introduced at some stage of the process.

31. The process of claim 30, wherein the treating in step d) is an acid treatment.

32. The process of claim 31, wherein the acid treatment comprises:
(i) adding an acid to the stream recovered in step c);
(ii) subjecting the reaction mixture of step (i) to distillation; and,
(iii) withdrawing a distillate comprising the solvent and containing less than 50 wppm nitrogen in the form of organic nitrogen compounds.

33. The process of claim 32, wherein the acid is a mineral acid.

34. The process of claim 33, wherein the mineral acid is selected from the group consisting of sulfuric acid and phosphoric acid.

35. The process of claim 32, wherein the acid is a carboxylic acid.

36. The process of claim 35, wherein the carboxylic acid is acetic acid.

37. The process of claim 31, wherein the acid treatment comprises:
(i) subjecting stream recovered in step c) to a continuously operated distillation;
(ii) feeding a stream comprising an acid at a point above a feed point of the stream recovered in step c) and
(iii) withdrawing a product stream comprising the polar solvent and containing less than 50 wppm nitrogen in the form of organic nitrogen compounds at a point above a feed point of the stream comprising an acid.

38. The process of claim 37, wherein the acid is a mineral acid.

39. The process of claim 38, wherein the mineral acid is selected from the group consisting of sulfuric acid and phosphoric acid.

40. The process of claim 37, wherein the acid is a carboxylic acid.

41. The process of claim 40, wherein the carboxylic acid is acetic acid.

42. The process of claim 31 wherein the acid treatment comprises treating the stream recovered in step c) with an acidic ion exchanger in its protonated form.

43. The process of claim 42, wherein the stream recovered in step c) is passed through a fixed bed containing the acidic ion exchanger.

44. The process of claim 42, wherein the acidic ion exchanger is a strongly acidic ion exchanger.

45. The process of claim 44, wherein the strongly acidic ion exchanger contains SO$_3$H groups.

46. The process of claim 42, wherein the acidic ion exchanger is a weakly acidic ion exchanger.

47. The process of claim 46, wherein the weakly acidic ion exchanger contains COOH groups.

48. The process of claim 30 further comprising:
f) at least partially condensing the overhead product from step c) to obtain a condensate containing, optionally after stripping out propene and any propane present

| | |
|---|---|
| 0–12 | wt. % propene, |
| 0–5 | wt. % propane, |
| 15–75 | wt. % propene oxide, |
| 20–85 | wt. % methanol and |
| 0–8 | wt. % water, | g) subjecting said condensate to an extractive distillation, by
g1) adding said condensate to a middle section of an extractive distillation column,
g2) adding an aqueous extraction solvent to the extractive distillation column at a point above a point at which the condensate enters,
g3) distilling off the propene oxide at head of the column,
g4) removing a bottom product containing methanol and water, and h) combining the bottom product from step c) with the bottom product from step g4) before subjecting it to step d).

49. The process of claim 48, wherein the extraction solvent in step g2) is an aqueous hydrazine solution containing from 0.5 to 5% by weight hydrazine.

50. The process of claim 30 further comprising in step d) subjecting the bottom product of step c) to hydrogenation before subjecting it to the treatment to remove organic nitrogen compounds.

51. The process of claim 48 further comprising in step d) subjecting the combined product of the bottom product of step c) and the product of step g4) to hydrogenation before subjecting it to the treatment to remove organic nitrogen compounds.

52. Process for the catalytic epoxidation of propene, wherein one or more nitrogen containing compounds are present or are introduced at some stage during the process, said process comprising:
a) in a reaction step reacting propene with hydrogen peroxide in the presence of a titanium silicalite catalyst and a solvent comprising methanol to obtain a product stream,
b) optionally passing the product stream from the reaction step to a pressure release step,
c) separating the product stream in a pre-evaporator having less than 20 theoretical separation stages into an overhead product containing propene, propene oxide and methanol, and into a bottom product containing methanol and water, wherein 20 to 60% of the total amount of methanol introduced with the product stream is being removed with the overhead product and the rest remaining in the bottom product,
d) treating at least a part of the bottom product from step c) to obtain a product containing less than 50 wppm nitrogen in the form of organic nitrogen compounds and, optionally after partially removing water from said treated product,
e) recycling at least a part of the treated product from step d) to the reaction step a).

* * * * *